United States Patent [19]

Leibinsohn

[11] 4,064,879
[45] Dec. 27, 1977

[54] PRESSURE-INDICATING SYRINGE

[75] Inventor: Saul Leibinsohn, Rishon Lezion, Israel

[73] Assignee: Metatech Corporation, Northbrook, Ill.

[21] Appl. No.: 674,283

[22] Filed: Apr. 6, 1976

[51] Int. Cl.² ............................................. A61M 5/00
[52] U.S. Cl. .................................. 128/215; 128/218 P
[58] Field of Search ........... 128/218 R, 218 C, 218 P, 128/218 PA, 218 F, 215, 216, 234, 220, 221

[56] References Cited
U.S. PATENT DOCUMENTS

| | | | |
|---|---|---|---|
| 1,039,591 | 9/1912 | Prideaux | 128/218 F |
| 1,123,990 | 1/1915 | Calhoun | 128/218 F |
| 3,162,217 | 12/1964 | Poli, Jr. et al. | 128/218 C X |
| 3,661,152 | 5/1972 | Beich et al. | 128/218 PA |
| 3,669,111 | 6/1972 | Dubner | 128/218 P |
| 3,831,602 | 8/1974 | Broadwin | 128/218 PA |

FOREIGN PATENT DOCUMENTS 97,164  6/1921  Switzerland ..................... 128/218 F Primary Examiner—John D. Yasko
Attorney, Agent, or Firm—Benjamin J. Barish

[57] ABSTRACT

A pressure-indicating syringe comprises a barrel, a plunger assembly movable therein and having an outer shaft and an inner piston, finger-engaging elements on the barrel and on the plunger shaft for moving the piston to inject fluid through an apertured end wall of the barrel, and an elastic connection between the finger-engaging elements of the plunger shaft and the piston enabling the piston to be displaced relative to the shaft an amount corresponding to the pressure on the piston during the injection of the fluid, thereby providing an indication of the injection pressure.

According to a further feature, the barrel includes a retaining member engagable with the plunger shaft for retaining the latter in an intermediate position with respect to the barrel, thereby enabling the device also to indicate a change in pressure in the injection compartment, and also to be used for applying a slow continuous injection.

19 Claims, 17 Drawing Figures

U.S. Patent  Dec. 27, 1977  Sheet 1 of 3  4,064,879
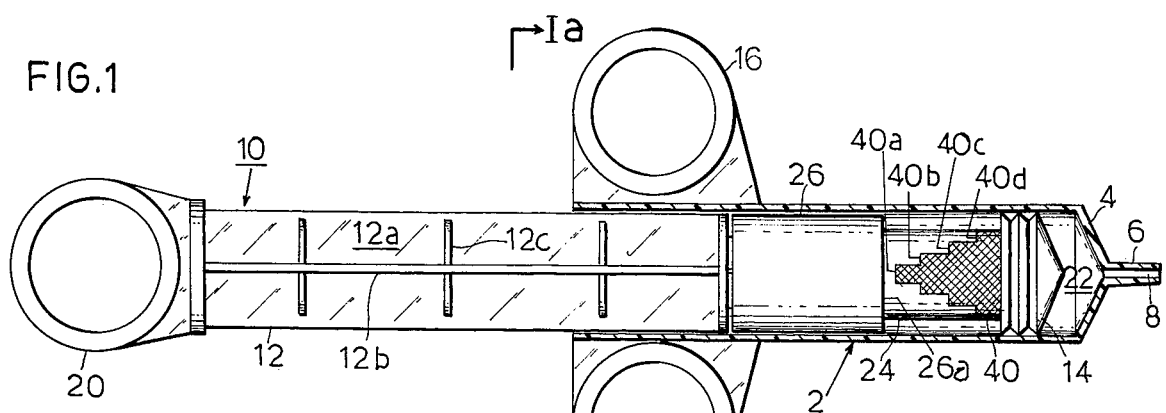
FIG.1
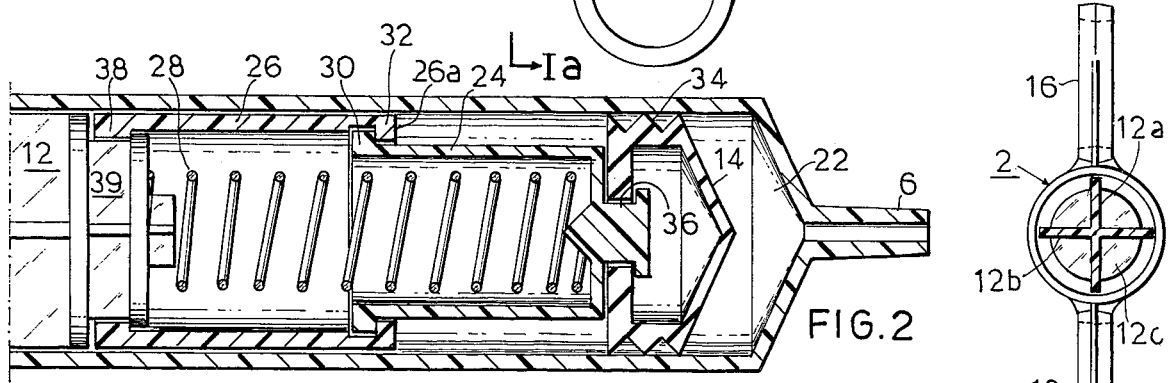
FIG.2
FIG.1a
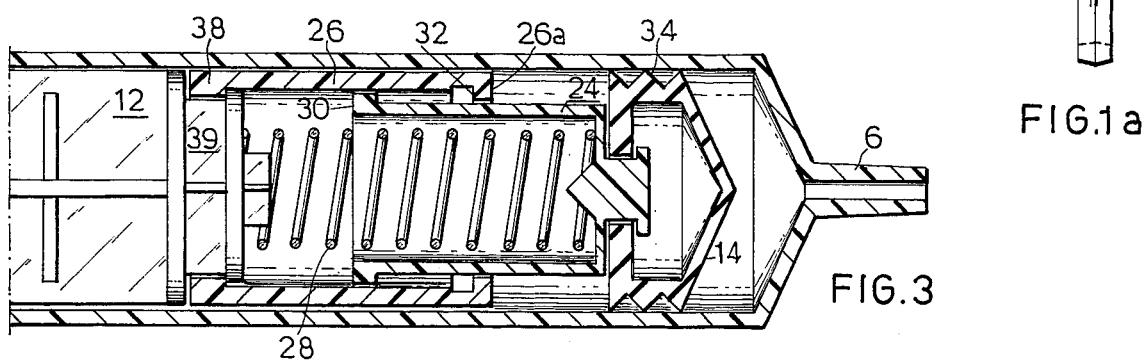
FIG.3
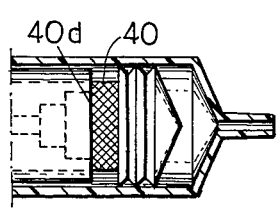
FIG.4
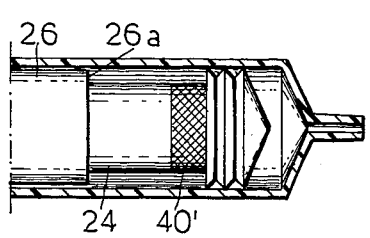
FIG.5
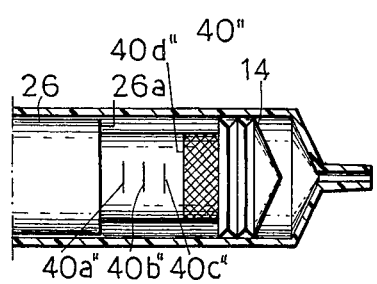
FIG.6

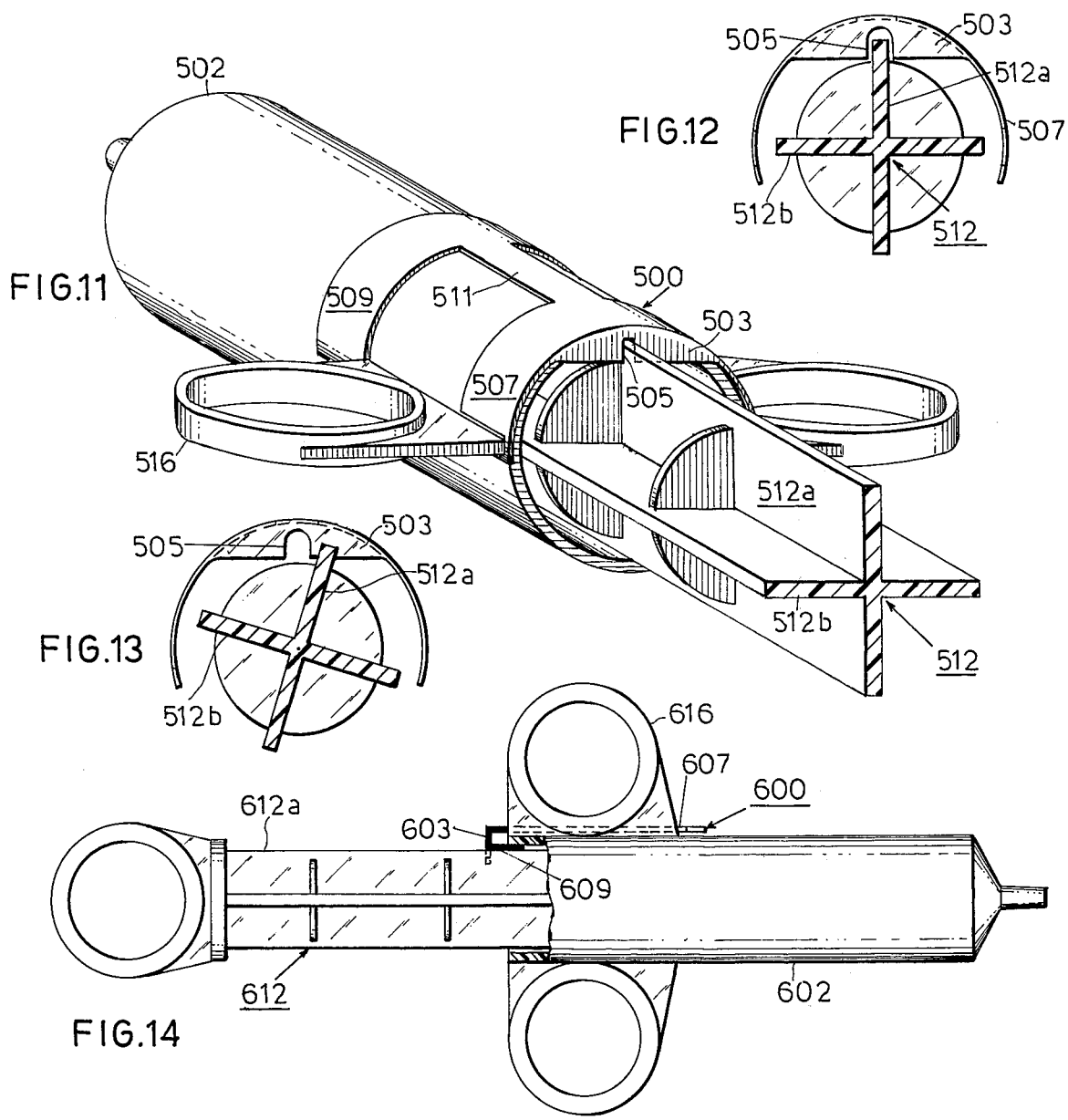

PRESSURE-INDICATING SYRINGE

BACKGROUND OF THE INVENTION

The present invention relates to syringes, particularly to syringes of the type including a barrel having an apertured end wall, a plunger assembly movably received within the barrel and including an outer shaft and an inner piston, and finger-gripping elements on the barrel and plunger shaft enabling the latter, and thereby the piston, to be manually moved towards the apertured end wall of the barrel for injecting fluid therethrough.

Devices of the foregoing type are commonly used as hypodermic syringes for injecting fluid into body cavities. Normally it is important, and sometimes quite critical, to inject the fluid at a predetermined pressure, which is usually determined by "feel". However, "feel" is far from satisfactory in many cases as it depends on the experience and skill of the user, and also on the peculiar parameters (e.g., size and sliding-friction of the piston) of the specific syringe being used. Some syringes are equipped with manometers for indicating the pressure of the fluid as it is being injected. However, manometers add substantially to the expense of the syringe; moreover, they are very awkward to use, and frequently the operator does not bother to use one even when available.

SUMMARY OF THE INVENTION

An object of the present invention is to provide a syringe of simple and inexpensive design capable of indicating pressure.

According to a broad aspect of the present invention, the syringe is provided with an elastic connection between the finger-engaging elements of the plunger shaft and of the piston enabling the piston to be displaced relative to the shaft finger-engaging element an amount corresponding to the pressure on the piston during the injection of the fluid. This displacement of the piston relative to the plunger shaft is indicated by indicium carried by the piston and viewable through the barrel, and thus provides an indication of the injection pressure. Accordingly, the user need only observe the position of the piston indicium carried by the during the injection process, which informs him of the pressure at which the fluid is being injected and thereby enables him to apply the required or optimum pressure for each case.

The invention may take a larger number of forms, some of which are described below for purposes of example.

According to one preferred embodiment described below, the elastic connection comprises a stem carrying the piston at one end, the opposite end of the piston stem being displacable with respect to the inner end of the plunger shaft; in addition, a spring is interposed between the piston and the inner end of the plunger shaft and biases the piston away from the shaft.

The piston stem preferably the indicium providing the indication of the injection pressure. In one described form, the indicium comprises a color band of stepped widths carried by the piston stem to indicate a plurality of injection pressures. According to another described form, the indicium comprises a color band of uniform width and of predetermined length carried by the inner end of the piston stem to indicate a single predetermined injection pressure. According to a still further described form, the indicium comprises a plurality of stripes or lines carried by the inner end of the piston stem to indicate a plurality of injection pressures.

According to another described embodiment, the elastic connection comprises an elastic bellows formed at the outer end of the piston and attached to the inner end of the plunger shaft. In this embodiment, the device preferably includes a fixed reference element fixed at the inner end of the plunger shaft and cooperable with the elastic bellows to provide an indication of the injection pressure.

Several further embodiments showing other forms of elastic connections are described below.

According to another aspect of the invention, the barrel includes a retaining member engagable with the plunger shaft for retaining the latter in an intermediate position with respect to the barrel. This aspect of the invention provides several additional advantages. One advantage is that it enables the syringe also to be used to indicate any drop in pressure in the fluid compartment of the syringe and in the device to which it is attached. Another advantage is that it enables the syringe to apply a continuous pressure to a fluid to be slowly injected into a body cavity, this being effected by locking the plunger shaft to the barrel whereby the pressurized piston applies a continuous (although decreasing) pressure to the fluid during the injection thereof.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a side elevational view of one form of syringe constructed in accordance with the invention, FIG. 1a being a sectional view along lines 1A—1A thereof;

FIG. 2 is an enlarged longitudinal sectional view of a portion of the syringe of FIG. 1;

FIGS. 3 and 4 are partial longitudinal sectional views illustrating the positions of the elements during use when full injection pressure is being applied;

FIGS. 5 and 6 are fragmentary views illustrating two variations in the indicium markings provided on the syringe of FIGS. 1-4;

FIGS. 11-13 illustrate the use of one form of retainer member for retaining the plunger shaft in an intermediate position with respect to the barrel;

and FIGS. 14-16 illustrate the use of another form of retainer member for retaining the plunger shaft in an intermediate position with respect to the barrel.

DESCRIPTION OF THE PREFERRED EMBODIMENTS

Figure 7:
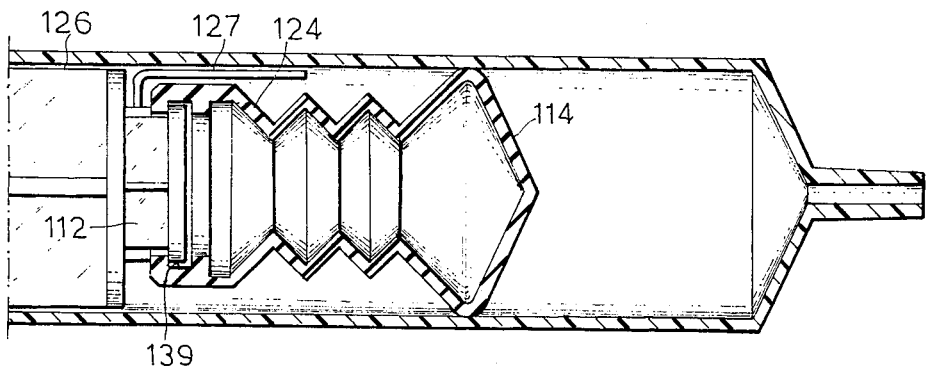
FIGS. 7-10 are partial longitudinal sectional views illustrating four further embodiments of syringes constructed in accordance with the invention.

FIGS. 1-4 illustrate the invention embodied in one known form of syringe. The syringe of this embodiment includes a cylindrical barrel, generally designated 2, having an end wall 4 terminating in a syringe tip 6 both of standard conical configuration, the syringe tip 6 being formed with an aperture 8 and adapted to receive a syringe needle or tube (not shown). Disposed within barrel 2 is a plunger assembly, generally designated 10, including a plunger shaft 12 extending through the outer open end of the barrel, and a piston 14 at its inner end. Barrel 2 is provided with a pair of finger-engaging elements in the form of loops 16 and 18, and the outer end of plunger shaft 12 is formed with a further finger-engaging element or loop 20. In use, the user inserts his thumb through plunger-shaft loop 20, and two of his fingers through barrel loops 16 and 18, and draws them together to move the plunger shaft 12 and piston 14 towards the barrel end wall 4 to cause the fluid, received within compartment 22 defined by piston 14 and the barrel end wall, to be pressure-injected through aperture 8 of syringe tip 6.

In the illustrated known construction, the plunger shaft 12 is constituted of two intersecting right-angle walls 12a, 12b, reinforced by circular strengthening ribs 12c, the outer ends of wall 12a and 12b slidingly engaging the inner cylindrical surface of barrel 2 for guiding the movement of the plunger assembly when it is manipulated by the user in the manner described above.

The syringe, insofar as described above, is well known and therefore further details of its construction are not deemed necessary.

In accordance with the present invention, the syringe is provided with an elastic connection between the finger-engaging loop 20 of plunger shaft 12, and the piston 14, enabling the piston to be displaced relative to the loop an amount corresponding to the pressure applied by piston 14 during the injection process, thereby providing an indication of the injection pressure.

In the embodiment of FIGS. 1-4, this elastic connection comprises a cylindrical stem 24 fixed at one end to piston 14, the opposite end of the stem being telescopingly received within a cylindrical sleeve 26 fixed to the end of plunger shaft 12. A spring 28 is interposed between piston 14 and the inner end of plunger shaft 12 and biases piston 14 away from the latter shaft, i.e. towards syringe tip 6. Piston stem 24 is formed with an out-turned annular flange 30 adapted to engage an in-turned annular flange 32 on sleeve 26 for limiting the outward movement of the piston 14 and its stem 24.

Piston 14 is preferably made of flexible rubber or synthetic elastomeric material and is formed with an outer corrugated surface 34 for sealingly engaging the inner surface of barrel 2. The piston may be snap-fitted onto an annular recess 36 formed at the end of stem 24. Sleeve 26 may be formed with an in-turned annular flange 38 snap-fitted into an annular recess 39 formed at the respective end of plunger shaft 12.

In use, the fluid (usually a liquid, but may also be a gas) is contained within compartment 22 between piston 14 and the syringe tip 6, and is ejected through aperture 8 of the syringe tip as manual pressure is applied between the finger-engaging loops 16, 18 and 20. During this ejection of the fluid from compartment 22, the pressure applied to piston 14 causes it and its cylindrical stem 24 to be displaced within sleeve 26 of the plunger shaft 12 against the action of spring 28, the amount of displacement corresponding to the pressure on piston 14, as shown in FIG. 3. Thus, by visually observing the position of piston stem 24 with respect to the end 26a of sleeve 26, the user is conveniently provided with an indication of the amount of pressure on piston 14, and he can therefore regulate the manual force he applied to plunger shaft 12 so as to produce a specified or optimum pressure during the injection process.

Piston stem 24 includes an indicium marking which, relative to the respective end 26a of sleeve 26 fixed to plunger shaft 12, provides an indication of the injection pressure. The indicium is shown in FIGS. 1 and 4 as comprising a color band 40 of stepped widths to indicate any one of a plurality of injection pressures. Thus, marking 40 could be provided so that the alignment of end 26a of sleeve 26 with the various stepped ends of indicium marking 40 indicates different fractions of a predetermined pressure, step 40a indicating one-fourth of full pressure, step 40b indicating one-half of full pressure, step 40c indicating three-fourths of full pressure, and step 40d indicating full pressure. Accordingly, if the user wishes to inject the fluid at a full predetermined pressure, he applies sufficient manual force to the plunger-shaft finger loop 20, with respect to the barrel finger loops 16 and 18, such that end 26a of sleeve 26 aligns with end 40d of the marking 40 on piston stem 24 as shown in FIG. 4, and he maintains this alignment during the injection process.

FIG. 5 illustrates a variation wherein the indicium marking comprises a color band 40' of uniform width and of predetermined length carried by the inner end of the piston stem 24 to indicate, relative to the inner end 26a of the plunger sleeve 26, a single predetermined injection pressure.

FIG. 6 illustrates another variation wherein the indicium marking 40' comprises a plurality of stripes or lines 40a" – 40d", preferably of different colors, to indicate any one of a plurality of injection pressures. Preferably lines 40a" – 40c", indicating partial pressures, are relatively short lines extending less than the full diameter of the cylindrical piston stem 24 and are formed on opposite sides of the stem; whereas line 40d", indicating full injection pressure, is formed around the complete diameter of the stem.

FIGS. 7-10 illustrate further embodiments of the invention.

In FIG. 7, the elastic connection between the plunger shaft 112 and its piston 114 comprises an elastic bellows 124 formed at the outer end of piston 114 and attached to the inner end of the plunger shaft. In this case, the latter end of bellows 124 is snap-fitted into an annular recess 139 carried on sleeve 126 fixed to the plunger shaft.

Sleeve 126 further includes a reference element 127, in the form of a finger, fixed to its inner end and cooperable with elastic bellows 124 to provide an indication of the injection pressure. Thus, by viewing the end of finger 127 with respect to bellows 124, the observer is informed of the pressure applied on piston 114 during the injection process. The outer surface of bellows 124 may carry markings (e.g. colored lines) to indicate this pressure, or the pressure may be indicated merely by the convolution of the bellow aligned with the end of finger 127. It will also be appreciated that indicator element 127 could be in the form of a sleeve instead of a finger.

Figure 8:
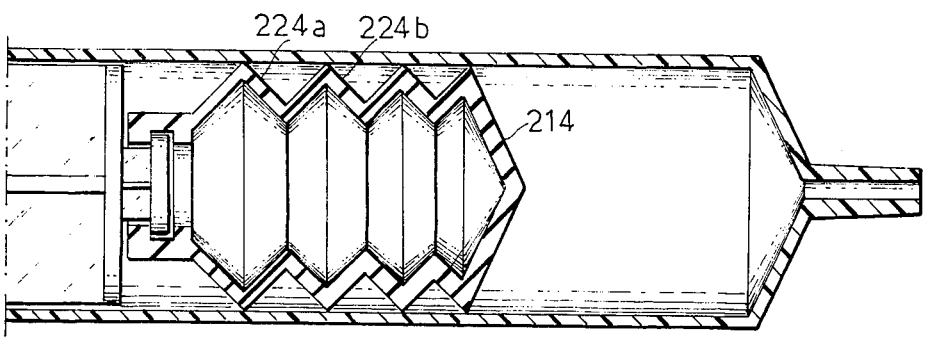

FIG. 8 illustrates a further variation wherein, instead of including indicator finger 127, the elastic bellows, therein shown as 224, is made of non-uniform thickness, being thinner at the plunger shaft end (left end in FIG. 8) then at the piston 214 end. Thus, as pressure is applied to the piston 214, the thinner end 224a first flexes and then the thicker end 224b flexes. As an example, the bellows can be designed so that at one-half pressure end 224a flexes, and at full pressure end 224b flexes.

Figure 9:
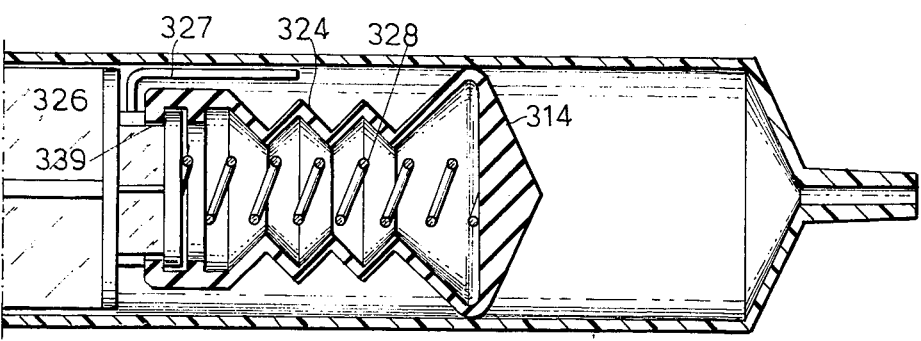

FIG. 9 illustrates a still further embodiment wherein the elastic connection includes a bellows 324 carried at the outer end of piston 314 and attached to the inner end of the plunger shaft, in this case being seated within annular recess 339 of plunger shaft sleeve 326. A spring 328 is enclosed within bellows 324 and is interposed between piston 314 and the inner end of plunger shaft sleeve 326. It will be appreciated that piston 314 will be displaced, in the same manner as described above, according to the pressure applied thereto during the injection process, and this displacement can be indicated to the user in any of the manners described above, for example by including a pressure indicating element 327 which could be in the form of a finger or a sleeve as described.

Figure 10:
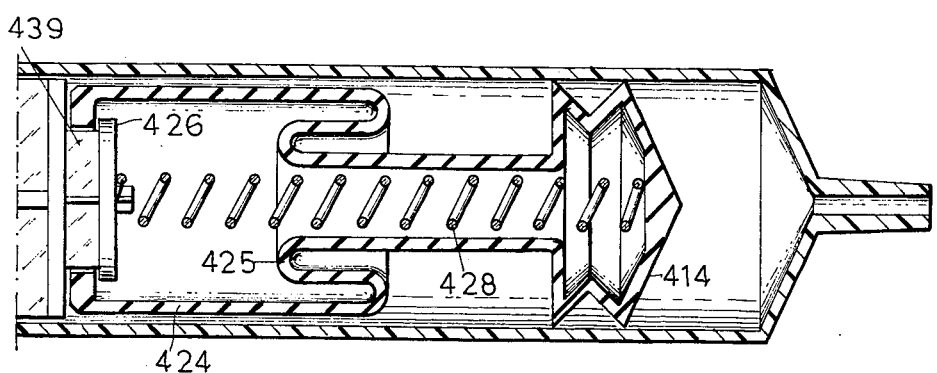

FIG. 10 illustrates a still further embodiment, wherein the piston 414 is integrally formed with its stem 424 except that the latter includes a flexible, looped, intermediate portion 425 to provide the elastic connection between the piston and the plunger shaft. A spring 428 is disposed within stem 424 to bias piston 414 outwardly, and the stem may be snap-fitted onto an annular recess 439 formed in the end of plunger shaft sleeve 426 as described above. Thus, piston 414 will be displaced towards plunger shaft sleeve 426 in accordance with the pressure applied to the face of the piston during the injection process. This displacement may be indicated to the user in any appropriate manner, for example one of the manners described above with respect to the other embodiments.

FIGS. 11–16 illustrate another aspect of the invention involving the use of a retainer member carried by the barrel and engagable with the plunger shaft for retaining the latter in an intermediate position with respect to the barrel. There are important advantages for such a feature as will be described more particularly below.

One form of retainer member is illustrated in FIGS. 11–13. This retainer member, generally designated 500, includes a bent-over tongue 503 formed with a central recess 505, the member being snap-fitted onto the syringe barrel 502 by means of a pair of curved arms 507 and 509 joined by web 511.

Retainer member 500 is preferably of resilient metal or plastic enabling it to be snap-fitted onto the barrel with the arms 507, 509 spaced longitudinally of the barrel. It is applied to the barrel so that its tongue 503 extends radially into the open end of the barrel where it cooperates with one of the right-angle walls 512a, 512b of the plunger shaft 512 to selectively retain the plunger in an intermediate position with respect to the barrel. In one angular position of the plunger shaft (FIG. 12), its wall is aligned with recess 505 of the retainer tongue 503, permitting the free movement of the plunger shaft axially within the barrel, but when the plunger shaft is angularly rotated, as shown in FIG. 13, a wall 512a of the plunger shaft wedges against the retainer tongue 503 to thereby lock the plunger shaft in that particular position within the barrel.

This simple feature provides a number of important advantages. One advantage is that it enables the syringe also to be used as an indicator to indicate any change in pressure within the fluid compartment of the syringe, or more important, within the device to which the syringe is attached. For example, such syringes are frequently used for inflating the seal around an endotracheal tube during the administration of anesthetic gases. Usually, the endotracheal tube seal is inflated to a predetermined pressure to seal the patient's trachea and close observation has to be exercised to make sure that the seal is maintained and that no gas is escaping between it and the patient's trachea. With the device of the present invention, including a retainer member as described above, the syringe can be used to inflate the seal to a predetermined pressure, and while the seal is kept connected to the syringe its plunger shaft can be locked to the barrel so that if there is any drop in pressure in the seal, the piston will be displaced under the action of its spring to indicate this drop in pressure. Another advantage in the use of the retainer arrangement is that it enables the syringe to be utilized for continuously injecting a fluid (for example into a muscle) at a slow rate, this being effected by locking the plunger shaft to the barrel and permitting the piston spring to effect the continuous, slow injection of the fluid.

FIGS. 14–16 illustrate another form of retainer member that may be used. In this case, the retainer member, generally designated 600 and a top plan view of which is shown in FIG. 15, includes an upper long arm 607 and a pair of lower short arms 609 which are spaced from the upper arm in the radial direction with respect to the syringe barrel 602 a distance slightly less than the thickness of the barrel wall so that the member can be snap-fitted onto the barrel by the arms 607, 609 gripping opposite sides of the barrel wall. Long arm 607 is bifurcated at its free end, as shown in FIG. 15, to enable it to straddle finger-engaging loop 616 of the barrel 602 and to engage its sides.

As in the FIGS. 11–13 embodiment, retainer member 600 includes a tongue 603 extending radially into the open end of the barrel, the tongue being formed with a central recess 605 (FIG. 16) which cooperates with a wall 612a of the plunger shaft 612 in the same manner as described above in FIGS. 11–13.

Many other variations can be made. For example, the plunger shaft could also be retained within the barrel by merely dimensioning the parts to provide friction between the two having a greater holding power than the spring or elastic means used between the piston and the plunger shaft.

Other variations, modifications and applications of the illustrated embodiments will be apparent.

What is claimed is:

1. A syringe comprising: a barrel having an apertured wall at one end and open at its opposite end; a plunger assembly movably received within the open end of the barrel; said plunger assembly including a shaft at its outer end, and a piston at its inner end defining a compartment with the barrel apertured wall for receiving a fluid to be injected through the aperture thereof; finger-gripping elements on the barrel and on the plunger shaft enabling the latter and the piston to be manually moved towards the apertured wall of the barrel for pressure-injecting fluid therethrough; an elastic connection between the finger-gripping element of the plunger shaft and the piston enabling the piston to be displaced relative to the shaft finger-gripping element an amount corresponding to the pressure on the piston during the injection of the fluid, and indicium carried by said piston and viewable through said barrel thereby providing a viewable indication of the injection pressure.

2. A syringe according to claim 1, wherein said elastic connection comprises a stem on said piston and displaceable with respect to the inner end of the plunger shaft, and a spring interposed between the piston and the inner end of the plunger shaft biasing the piston away therefrom.

3. A syringe according to claim 2, wherein said piston stem is telescopingly received within the inner end of the plunger shaft.

4. A syringe according to claim 2, wherein said indicium is carried by said piston stem includes indicium related to the plunger shaft to provide an indication of said injection pressure.

5. A syringe according to claim 4, wherein said indicium comprises a color band of stepped widths carried by the piston stem to indicate, relative to the inner end of the plunger shaft, a plurality of injection pressures.

6. A syringe according to claim 4, wherein said indicium comprises a color band of predetermined length carried by the piston stem to indicate, relative to the inner end of the plunger shaft, a single predetermined injection pressure.

7. A syringe according to claim 4, wherein said indicium comprises a plurality of stripes carried by the piston stem to indicate, relative to the inner end of the plunger shaft, a plurality of injection pressures.

8. A syringe according to claim 2, wherein said plunger shaft includes a cylindrical sleeve at its inner end for telescopingly receiving the piston stem.

9. A syringe according to claim 1, wherein said elastic connection comprises an elastic bellows formed at the outer end of the piston and attached to the inner end of the plunger shaft.

10. A syringe according to claim 9, further including a fixed reference element fixed to the inner end of the plunger shaft and cooperable with said elastic bellows to provide an indication of the injection pressure.

11. A syringe according to claim 9, wherein the wall thickness of said elastic bellows is non-uniform, being thinner at the plunger shaft end and thicker at the piston end, whereby the non-uniform flexing of the elastic bellows provides an indication of the injection pressure.

12. A syringe according to claim 1, wherein said elastic connection comprises a bellows carried at the outer end of the piston and attached to the inner end of the plunger shaft, and a spring enclosed by the bellows and interposed between the plunger shaft and the piston.

13. A syringe according to claim 1, wherein the piston includes a stem fixed to the plunger shaft, said stem including a flexible intermediate portion constituting said elastic connection.

14. A syringe according to claim 1, wherein the barrel includes a retaining member engagable with the plunger shaft for retaining the latter in an intermediate position with respect to the barrel.

15. A syringe according to claim 14, wherein said retaining member comprises a tongue cooperable with the plunger shaft such that in one angular position of the plunger shaft with respect to the barrel, the tongue permits the axial movement of the plunger shaft within the barrel, but in another angular position of the plunger shaft, the tongue engages the plunger shaft and retains same against axial movement within the barrel.

16. A syringe according to claim 14, wherein said locking member comprises a clip for removably attaching same to the barrel.

17. A syringe according to claim 16, wherein said clip includes a pair of curved arms spaced axially with respect to the barrel and adapted to be snap-fitted thereon.

18. A syringe according to claim 16, wherein said clip includes a pair of arms spaced radially with respect to the barrel an amount slightly less than the thickness of the barrel wall and adapted to be snap-fitted thereto.

19. A syringe according to claim 2 wherein the plunger assembly is frictionable movable with respect to the barrel to produce a frictional holding force greater than that of said spring so as to frictionally retain the plunger assembly in any moved position within the barrel.

* * * * *